United States Patent [19]

Ohashi et al.

[11] Patent Number: 5,552,445
[45] Date of Patent: Sep. 3, 1996

[54] COMPOSITION FOR EXTERNAL SKIN CARE

[75] Inventors: Yukihiro Ohashi, Utsunomiya; Taketoshi Fujimori; Minoru Nagai, both of Ichikaimachi; Akira Kawamata, Utsunomiya; Yukihiro Yada, Ninomiyamachi; Kazuhiko Higuchi, Ichikaimachi; Genji Imokawa, Utsunomiya; Yoshinori Takema, Ichikaimachi; Yukiko Sakaino, Utsunomiya; Ayumi Ogawa, Motegimachi; Tsutomu Fujimura, Ichikaimachi, all of Japan

[73] Assignee: Kao Corporation, Tokyo, Japan

[21] Appl. No.: 211,052

[22] PCT Filed: Sep. 22, 1992

[86] PCT No.: PCT/JP92/01210

§ 371 Date: Mar. 23, 1994

§ 102(e) Date: Mar. 23, 1994

[87] PCT Pub. No.: WO93/05763

PCT Pub. Date: Apr. 1, 1993

[30] Foreign Application Priority Data

Sep. 24, 1991 [JP] Japan .................... 3-243669
May 22, 1992 [JP] Japan .................... 4-130699

[51] Int. Cl.$^6$ ................................ A61K 31/13
[52] U.S. Cl. ............. 514/669; 514/844; 514/845; 514/873; 564/507
[58] Field of Search ............ 514/669, 873, 514/844, 845; 564/507

[56] References Cited

U.S. PATENT DOCUMENTS 3,766,267 10/1973 Zak et al. .................... 514/873
4,734,277 3/1988 Login ........................ 514/873
5,194,252 3/1993 Hofmann .................... 514/873
5,380,528 1/1995 Alban et al. ................ 514/873

FOREIGN PATENT DOCUMENTS 0282816  9/1988  European Pat. Off. .
54-117421  9/1979  Japan .
54-135233 10/1979  Japan .
54-147937 11/1979  Japan .
WO92/06982  4/1992  WIPO .

Primary Examiner—Shelley A. Dodson
Attorney, Agent, or Firm—Oblon, Spivak, McClelland, Maier & Neustadt, P.C.

[57] ABSTRACT

A composition for external skin care comprising an amine derivative represented by the following formula (1),

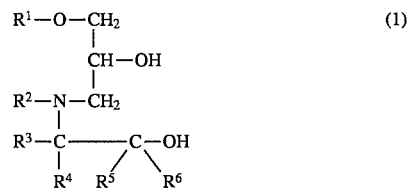

wherein $R^1$ is a linear, branched, or cyclic saturated or unsaturated hydrocarbon group having 4–40 carbon atoms, and $R^2$, $R^3$, $R^4$, $R^5$ and $R^6$ are individually a hydrogen atom or a hydrocarbon group having 1–10 carbon atoms, which may be substituted or unsubstituted by 1 or more hydroxy groups; or an acid addition salt thereof, in an amount from 0.0001 to less than 0.1% by weight; and a method of curing wrinkles and keratinization of the skin characterized by applying said amine derivative or its salt to the skin.

8 Claims, 3 Drawing Sheets

COMPOSITION FOR EXTERNAL SKIN CARE

FIELD OF THE INVENTION

The present invention relates to a composition for external skin care which enables the skin to maintain its normal functions and has an effect of curing keratinization and wrinkles of the skin.

BACKGROUND ART

The skin prevents water and other various components in living bodies from being lost. It plays roles of preventing water from dissipating and of constantly maintaining a body temperature. Skin also functions as a barrier for protecting bodies from external physical and chemical stimulators (e.g., humidity, temperature, ultraviolet rays, etc.) and from various bacteria. Its physiological functions in the activities of living bodies are therefore very important. Keeping healthy and beautiful skin is also a subject of a great concern, especially, for female. Conditions of skin, however, are constantly affected by various factors such as humidity, temperature, ultraviolet rays, cosmetics, age, diseases, stress, food customs, and the like. A number of skin troubles, such as deterioration of various skin functions, aging of the skin, and the like, are caused by these factors. Among these, troubles such as dry skin, fatty skin, dandruff, and the like are caused by thickening of the skin, incomplete keratinization, abnormal lipid metabolism, and the like resulting from the progress in turnover of epidermis which is induced by external and internal factors affecting the skin.

Major conventional methods of preventing the skin troubles and improving the skin have been preventing the skin from drying or promoting its moisture retention capability by the application of synthetic or natural moisturizing components, improving blood circulation in the skin by the application of blood circulation promoters, and the like.

These methods, however, involve various problems relating to their effects on the skin trouble prevention or the skin improvement, duration for which the effects last, stability and safety of drugs, and the like.

Development of a composition for external skin care which is safe and has a superior keratin improving effect has therefore been desired.

On the other hand, wrinkles are produced by aging of the skin due to senility, exposure to sun light, and the like. Cells constituting fibroblost synthesizing dermal fiber components decrease and become small due to exposure to sun light and along with age. Especially, a large amount of colagen fibers are lost, leading to dermal degeneration and reduction in the dermal fat organization, and finally to the skin aging. This is a major cause of wrinkles, atony, and loss of flexibility.

A number of compositions and methods have been proposed for suppressing or curing aged skins such as wrinkles and the like (Japanese Patent Laid-open (ko-kai) Nos. 185005/1987, 502546/1987, 72157/1990, 288822/1990, etc.). Most of them, however, are not satisfactory in their effects of wrinkle improvement.

Vitamin A acid has been confirmed to exhibit a wrinkle curing effect [Journal of the American Academy of Dermatology, Vol. 25, No. 2, Part 1, 231–237 (August, 1991); ibid. Vol. 21, No. 3, Part 2, 638–644 (September, 1989); ibid. Vol. 19, No. 1, Part 2, 169–175 (July 1988); ibid. Vol. 15, No. 4, Part 2, (October, 1986)]. Vitamin A acid, however, has problems in its safety; e.g., it induces red spots on the skin, is irritative and teratogenic.

Development of a safe composition for external skin care exhibiting an excellent wrinkle curing effect has therefore been desired.

Some compounds among amine derivatives represented by the following formula (1),

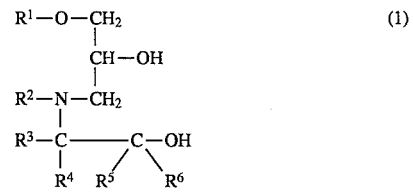

(wherein $R^4$ is a linear, branched, or cyclic saturated or unsaturated hydrocarbon group having 4–40 carbon atoms, and $R^2$, $R^3$, $R^4$, $R^5$, and $R^6$ are individually a hydrogen atom or a hydrocarbon group having 1–10 carbon atoms, either substituted or unsubstituted by 1 or more hydroxy groups) are known to be useful as an emulsifier [Journal of Colbid and Interface Science, Vol. 64, No. 2, 300–310 (1978), Japanese Patent Laid-open (ko-kai) No. 117421/1979]. It is also known that these compounds may be added to cosmetic compositions in an amount of 0.1–30% by weight [Japanese Patent Laid-open (ko-kai) Nos. 135233/1979 and 147937/1979]. However, there are no knowledge about the actions of said compounds (1) to the skin; especially their actions effected to dermal cells in the skin have not been known at all.

Based on the supposition that the wrinkles and keratinization of the skin are produced by abnormalities in functions of the skin organization, which are caused by various factors externally or internally affecting living bodies, such as environmental changes, e.g., change of climate, ultraviolet rays, etc., variations in physiological functions, e.g., those due to aging, diseases, etc.), the present inventors have studied various compounds as to (1) their capability of suppressing the progress in epidermal turnover, resulting in skin thickening, incomplete keratinization, abnormal lipid metabolism, etc., which are caused by ultraviolet rays, various components, etc.; and their capability of normalizing the keratinized skin, (2) their wrinkle improving capability, (3) their safety, and the like. As a result, the present inventors have found that amine derivatives of the above formula (1) and their acid addition salts exhibit these capabilities even in a very small amount, and thus are useful as a component for compositions to be applied externally to the skin. The findings have led to the completion of the present invention.

DISCLOSURE OF THE INVENTION

The present invention relates to a composition for external skin care comprising 0.0001–0.1% by weight of an amine derivative of the above formula (1) or its acid addition salt.

The present invention also relates to a method of improving wrinkles characterized by applying said amine derivative or its acid addition salt to the skin.

Furthermore, the present invention relates to a method of improving keratinization of the skin characterized by applying said amine derivative or its acid addition salt to the skin.

BEST MODE FOR CARRYING OUT THE INVENTION

Figure 1:
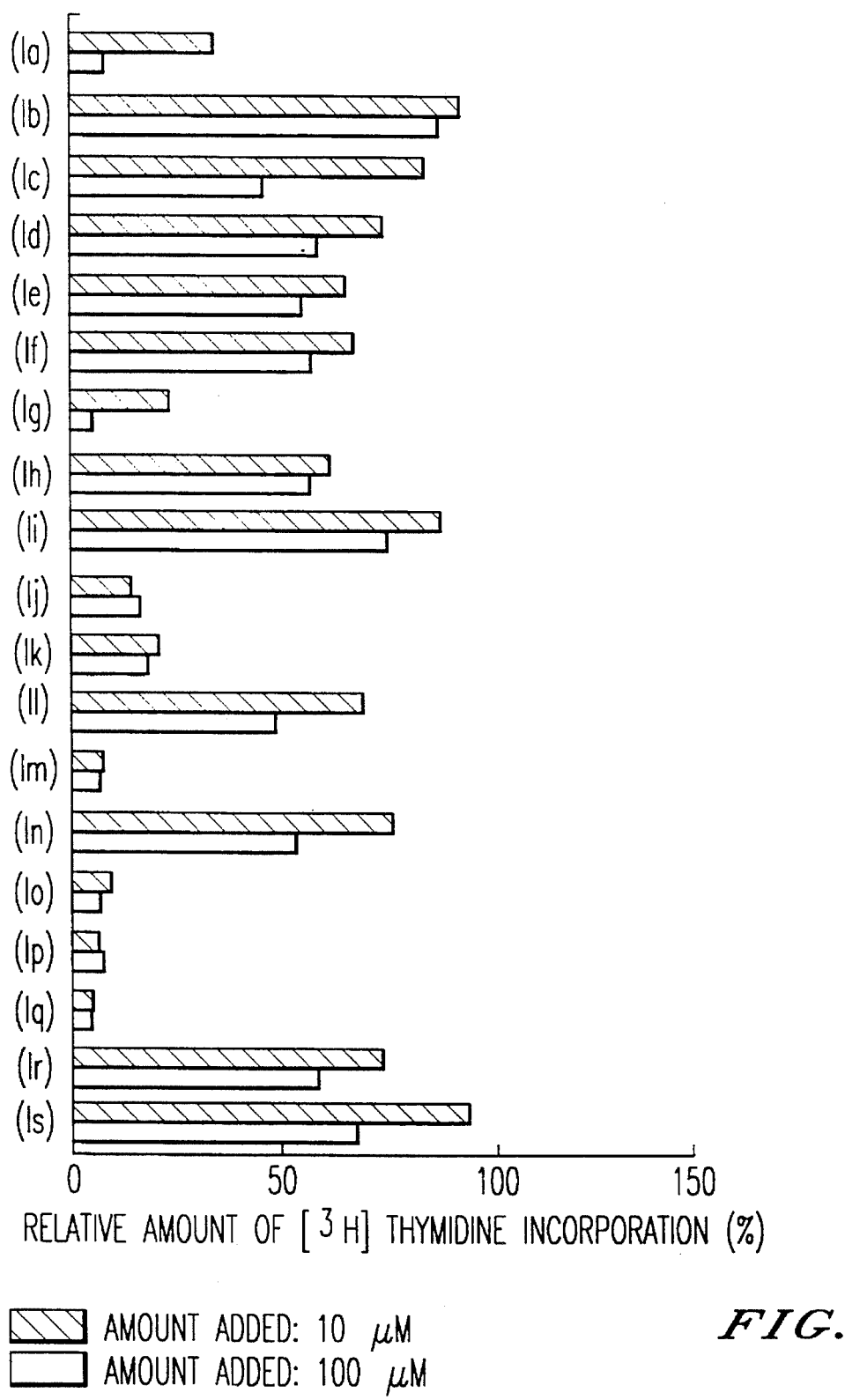
FIGS. 1 and 2 are drawings showing changes in the relative amount of [$^3$H] thymidine incorporation due to the addition of the amine derivative of Example 1.

In amine derivatives of formula (1), $R^1$ represents a linear, branched, or cyclic saturated or unsaturated hydrocarbon group having 4–40 carbon atoms. Specific examples include hydrocarbon groups such as butyl, hexyl, octyl, decyl, dodecyl, tetradecyl, pentadecyl, hexadecyl, octadecyl, docosyl, dotriacontyl, methyl-branched isostearyl, 2-ethylhexyl, 2-heptylundecyl, 5,7,7-trimethyl-2-(1,3,3-trimethylbutyl)-octyl, 9-octadecenyl, 9,12-octadecadienyl, cyclohexyl, phenyl, benzyl, cholesteryl, and the like. $R^2$, $R^3$, $R^4$, $R^5$ and $R^6$ individually represent a hydrogen atom or a hydrocarbon group having 1–10 carbon atoms, which may be substituted or unsubstituted by 1 or more hydroxy groups. Specific examples are hydrogen atom and hydrocarbon groups such as methyl, ethyl, butyl, hexyl, phenyl, benzyl, hydroxymethyl, hydroxyethyl, 1,2-dihydroxyethyl, 1,2,3-trihydroxypropyl, 1,2,3,4-tetrahydroxybutyl, 1,2,3,4,5-pentahydroxypentyl, and the like.

Among these amine derivatives (1), those having a linear, branched, or cyclic saturated or unsaturated hydrocarbon group having 4–40 carbon atoms for $R^1$, a hydrogen atom, a lower alkyl, or a lower hydroxyalkyl for $R^2$, and hydrogen atoms for $R^3$, $R^4$, $R^5$, and $R^6$ are preferable.

As preferable examples of $R^1$, linear, branched, or cyclic alkyl or alkenyl groups having 4–40 carbon atoms are given, and among them, especially preferred are methyl-branched alkyl groups of the following formula,

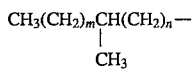

wherein m+n is 11–17, m is 4–10, n is 5–11. Particularly preferred are mixtures of compounds (described at Synthetic Example 3) of formula (1) having the above methyl-branched alkyl groups for $R^1$, in which m+n is 11–17, m is 4–10 and n is 5–11, with the distribution peak at m=7 and n=8.

Amine derivatives (1) of the present invention can be synthesized by various methods known in the art. For example, they can be synthesized by the addition of an amine derivative (3) to a glycidyl ether derivative (2) according to the following reaction formula.

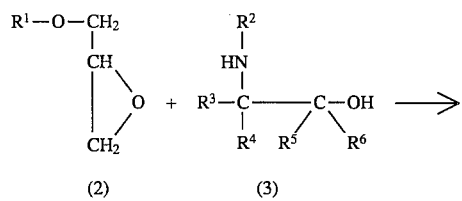

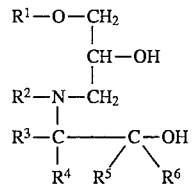

wherein $R^1$, $R^2$, $R^3$, $R^4$, $R^5$, and $R^6$ have the same meanings as defined above.

As required, the amine derivative (1) thus obtained can be converted into a salt of inorganic acid, e.g., hydrochloric acid, sulfuric acid, nitric acid, phosphoric acid, etc., or a salt of organic acid, e.g., succinic acid, fumaric acid, hexadecanoic acid, octadecanoic acid, lactic acid, glycolic acid, citric acid, tartaric acid, benzoic acid, etc., according to a conventional method.

These amine derivatives (1) and their acid addition salts exhibit actions of suppressing production of wrinkles and extinguishing wrinkles, as shown in Examples hereinafter.

Furthermore, as shown in Examples hereinafter, said amine derivatives (1) and their acid addition salts exhibit excellent effects of controlling synthesis of epidermal cell DNA, exhibiting, in both in vivo and in vitro experiments, their differentiation inducing activity and epidermal thickening controlling effects. Therefore, they possess an action of normalizing abnormal keratinization of epidermal cells in the skin.

Although said amine derivatives (1) and their acid addition salts may exhibit their effects by oral administration, a more desirable method for curing wrinkles and keratinization is to apply their effective amounts to the skin.

In the case where said amine derivative (1) or its acid addition salt is used by applying it to the skin, it is desirable that the compound be formulated into a composition for external skin care in an amount of from 0.0001 to less than 0.1% by weight and the composition be applied to the skin. The composition for external skin care may take various forms for use, such as pharmaceutical compositions for external skin care, cosmetics, and the like. Given as examples of pharmaceutical compositions for external skin care are various ointment compositions comprising the amine derivative (1) or its acid addition salt and other pharmaceutical components. As ointments, both those containing an oily base as a base and those containing an oil-in-water or water-in-oil emulsion-type base as a base can be used. There are no limitations as to the types of oily bases. Examples include vegetable oils, animal oils, synthetic oils, fatty acids, natural or synthetic glycerides, and the like. No special limitations are imposed to said other pharmaceutical components. For example, analgesic and antiphlogistic agents, antipruritics, disinfectants, astringents, emollients, hormones, vitamins, and the like may be used suitably as needed.

Where used as a cosmetic composition, it is possible to incorporate any commonly used cosmetic components, such as oils, moisturizers, UV absorbents, alcohols, chelating agents, pH modifiers, preservatives, thickeners, coloring agents, perfumes, and the like, in any optional combinations.

Cosmetic compositions may be prepared into a various forms depending on their uses; they may be water-in-oil or oil-in-water type emulsified cosmetics, creams, cosmetic milky lotions, lotions, oily cosmetics, facial packs, foundations, or the like. These compositions for external skin care may be prepared into the above various forms according to conventional methods.

EXAMPLES

The present invention is hereinafter described in detail by way of examples, which should not be construed to be limiting thereof.

Synthetic Example 1

Synthesis of 1-(2-hydroxyethylamino)-3-tetradecyloxy-2-propanol [In formula (1), $R^1=C_{14}H_{29}-$, $R^2=R^3=R^4=R^5=R^6=H$]

To a 3 1 5-necked flask equipped with a stirrer, dropping funnel, thermometer, nitrogen inlet tube, and condenser were charged 916.2 g (15 mol) of ethanolamine, and 183 g of ethanol. 270.5 g (1 mol) of tetradecylglycidyl ether was dropped to the mixture over 3 hours, while stirring and heating at 80° C. under a nitrogen atmosphere. After the addition, the ethanol and excess ethanolamine were removed by evaporation under reduced pressure. The residue was crystallized from methanol to obtain 295.7 g of colorless powder of the title compound (1a) (yield: 89.2%).

$$C_{14}H_{29}O-CH_2-CH(OH)-CH_2-NH-CH_2CH_2-OH \quad (1a)$$

Synthetic Example 2

Amine derivatives (1b)–(1f) were prepared in the same manner as in Synthetic Example 1.

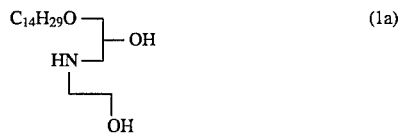
(1b)

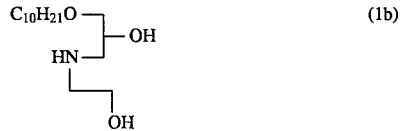
(1c)

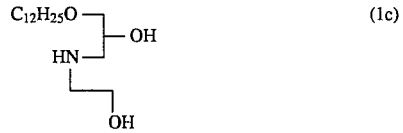
(1d)

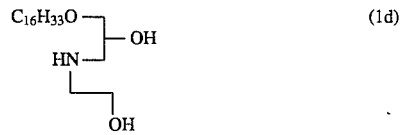
(1e)

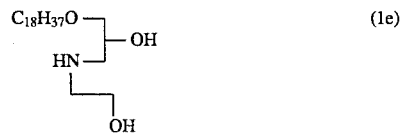
(1f)

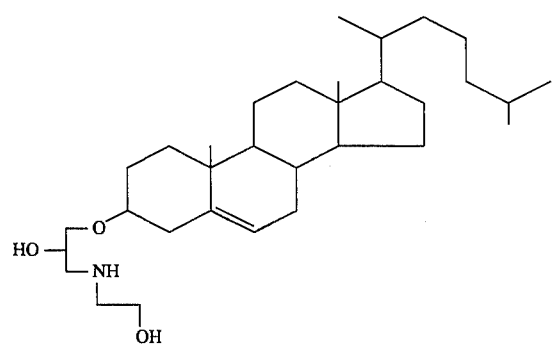

Synthetic Example 3

Synthesis of 1-(2-hydroxyethylamino)-3-(methyl-branched-isostearyl)-2-propanol [In formula (1), $R^1$=methyl-branched-isostearyl, $R^2=R^3=R^4=R^5=R^6=H$]

To a 3 1 5-necked flask equipped with a stirrer, dropping funnel, thermometer, nitrogen inlet tube, and condenser were charged 916.2 g (15 mol) of ethanolamine, and 183 g of ethanol. 326.6 g (1 mol) of methyl-branched-isostearylglycidyl ether was dropped to the mixture over 3 hours, while stirring and heating at 80° C. under a nitrogen atmosphere. After the addition, the ethanol and the excess ethanolamine were removed by evaporation under reduced pressure. The residue was purified by silica gel flush chromatography to obtain 320.5 g of light yellow paste of the title compound (1 g) (yield: 82.7%).

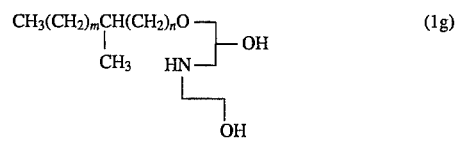
(1g)

wherein m+n is 11–17, m is 4–10 and n is 5–11, with the distribution peak at m=7 and n=8.

Synthetic Example 4

Synthesis of 1-(2-hydroxyethylamino)-3-(methyl-branched-isostearyl)-2-propanol hydrochloride 2.83 ml (34 mmol) of 12N hydrochloric acid was added to a solution of 13.2 g (34 mmol) of amine derivative (1 g) prepared in Synthetic Example 3 in 100 ml of ethanol, followed by evaporation of the solvent, to prepare 14.4 g of light yellow gel of the title hydrochloride (1 g') of amine derivative (1 g).

Synthetic Example 5

1-(2-hydroxyethylamino)-3-(9-octadecenyloxy)-2-propanol (1 h) was prepared in the same manner as in Synthetic Example 3.

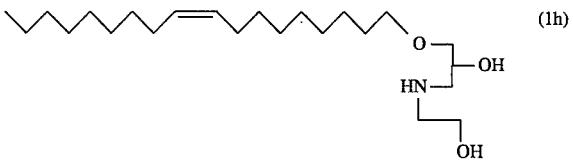
(1h)

Synthetic Example 6

Synthesis of 1-(2-hydroxyethylamino)-3-phenyloxy-2-propanol [In formula (1), $R^1$=phenyl, $R^2=R^3=R^4=R^5=R^6=H$]

To a 500 ml 4-necked flask equipped with a stirrer, dropping funnel, thermometer, nitrogen, inlet tube, and condenser were charged 91.6 g (1.5 mol) of ethanolamine and 20 g of ethanol. 15.0 g of phenylglycidyl ether was dropped to the mixture over 2 hours, while stirring and heating at 80° C. under a nitrogen atmosphere. After the addition, the ethanol and the surplus ethanolamine were evaporated under reduced pressure. The residue was subjected to vacuum distillation (175°–180° C. 0.5 Torr) to obtain 18 5 g of colorless solid of the title compound (1i) (yield: 86.7%).

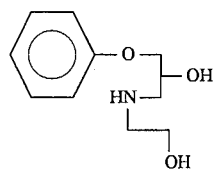
(1i)

Synthetic Example 7

Synthesis of 1-[bis(hydroxyethylamino)]-3-tetradecyloxy-2-propanol [In formula (1), $R^1=C_{14}H_{29}-$, $R^2=-CH_2CH_2OH$, $R^3=R^4=R^5=R^6=H$]

To a 1 l 5-necked flask equipped with a stirrer, dropping funnel, thermometer, and nitrogen inlet tube were charged 105.1 g (1 mol) of diethanolamine and 100 g of ethanol. 270.5 g of tetradecylglycidyl ether was dropped to the mixture over 30 minutes, while stirring and heating at 80° C. under a nitrogen atmosphere. After the addition, the mixture was stirred for a further 6 hours. The reaction mixture thus prepared was purified by silica gel flush chromatography to obtain 232.0 g of light yellow oil of the title compound (1j) (yield: 61.8%).

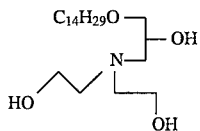
(1j)

Synthetic Example 8

Amine derivatives (1k)–(1c) were prepared in the same manner as in Synthetic Example 7.

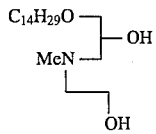
(1k)

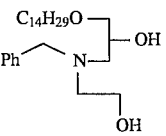
(1l)

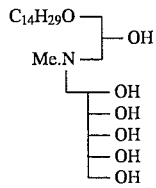
(1m)

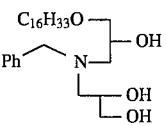
(1n)

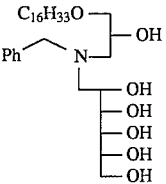
(1o)

Synthetic Example 9

Synthesis of 1-(2,3-dihydroxypropylamino)]-3-tetradecyloxy-2-propanol (1p) [In formula (1), $R^1=C_{14}H_{29}-$, $R^2=R^3=R^4=R^5=H$, $R^6=-CH_2OH$]

To a 2 l 4-necked flask equipped with a stirrer, dropping funnel, thermometer, and nitrogen inlet tube were charged 25 g (0.27 mol) of 3-amino-1,2-propanediol and 100 g of ethanol. 9.9 g (0.037 mol) of tetradecylglycidyl ether was dropped to the mixture over 3 hours, while stirring and heating at 80° C. under a nitrogen atmosphere. After the addition, the mixture was stirred for a further 1 hour. 1 l of water was added to the reaction mixture thus prepared to obtain a solid material by filtration. The solid was crystallized from methanol to obtain 10.3 g of colorless powder of the title compound (1p) (yield: 77.8%).

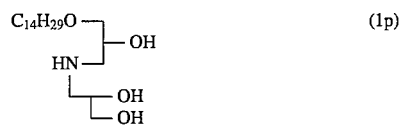
(1p)

Synthetic Example 10

Amine derivatives (1q)–(1s) were prepared in the same manner as in Synthetic Example 9.

(1q)

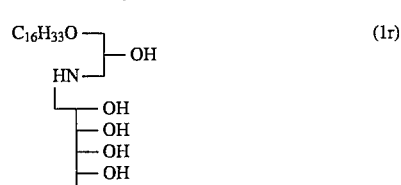
(1r)

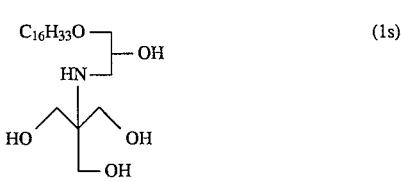
(1s)

Synthetic Example 11

Amine derivatives (1t)–(1x) were prepared in the same manner as in Synthetic Example 1.

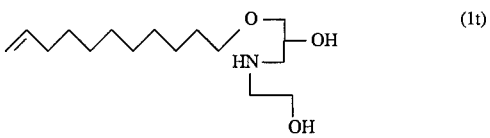
(1t)

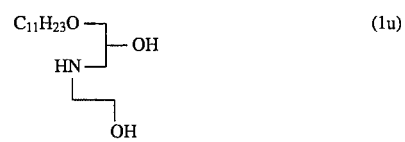
(1u)

-continued

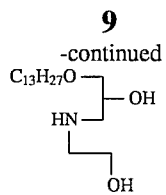 (1v)

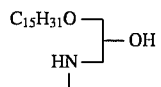 (1w)

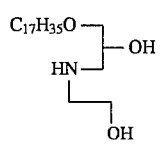 (1x)

Synthetic Example 12

Amine derivatives (1y)–(1z) were prepared in the same manner as in Synthetic Example 3.

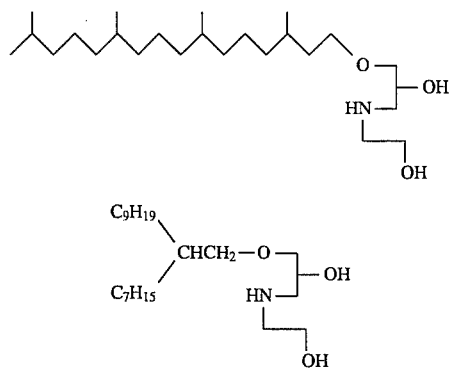

Synthetic Example 13

Amine derivatives (1aa)–(1ab) were prepared in the same manner as in Synthetic Example 7.

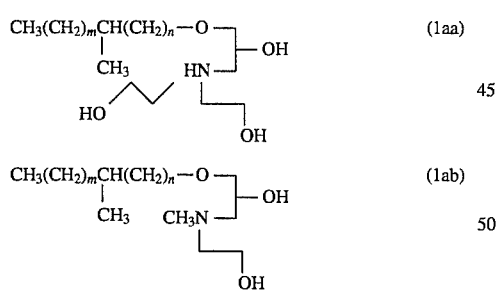

-continued

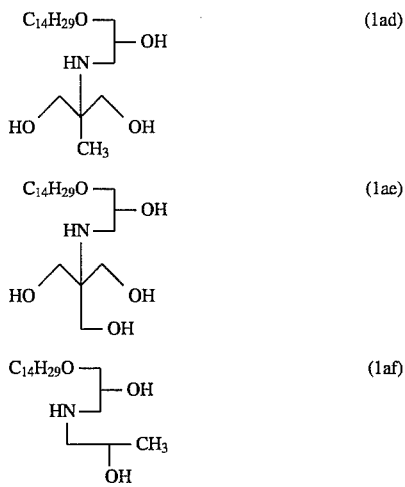

In the above formulas (1aa)–(1ac), m+n is 11–17, m is 4–10 and n is 5–11, with the distribution peak at m=7 and n=8.

Synthetic Example 14

Amine derivatives (1ad)–(1af) were prepared in the same manner as in Synthetic Example 9.

Substituents $R^1$–$R^6$ in amine derivatives of formulas (1a)–(1af) are listed in Tables 1–3.

TABLE 1

| Compound | Substituent | | | | | |
|---|---|---|---|---|---|---|
| | $R^1$ | $R^2$ | $R^3$ | $R^4$ | $R^5$ | $R^6$ |
| (1a) | $C_{14}H_{29}$ | H | H | H | H | H |
| (1b) | $C_{10}H_{21}$ | H | H | H | H | H |
| (1c) | $C_{12}H_{25}$ | H | H | H | H | H |
| (1d) | $C_{16}H_{33}$ | H | H | H | H | H |
| (1e) | $C_{18}H_{37}$ | H | H | H | H | H |
| (1f) | cholesteryl | H | H | H | H | H |

TABLE 1-continued

| Compound | R¹ | R² | R³ | R⁴ | R⁵ | R⁶ |
|---|---|---|---|---|---|---|
| (1g) | methyl-branched isostearyl | H | H | H | H | H |
| (1h) | oleyl | H | H | H | H | H |
| (1i) | phenyl | H | H | H | H | H |
| (1j) | $C_{14}H_{29}$ | $-CH_2CH_2OH$ | H | H | H | H |
| (1k) | $C_{14}H_{29}$ | $CH_3$ | H | H | H | H |
| (1l) | $C_{14}H_{29}$ | $-CH_2-$phenyl | H | H | H | H |

TABLE 2

| Compound | R¹ | R² | R³ | R⁴ | R⁵ | R⁶ |
|---|---|---|---|---|---|---|
| (1m) | $C_{14}H_{29}$ | $CH_3$ | H | H | $-CH(OH)-CH(OH)-CH(OH)-CH_2-OH$ | H |
| (1n) | $C_{16}H_{33}$ | $-CH_2-$phenyl | H | H | $-CH_2-OH$ | H |
| (1o) | $C_{16}H_{33}$ | $-CH_2-$phenyl | H | H | $-CH(OH)-CH(OH)-CH(OH)-CH_2-OH$ | H |
| (1p) | $C_{14}H_{29}$ | H | H | H | $-CH_2OH$ | H |
| (1q) | $C_{16}H_{33}$ | H | H | H | $-CH_2OH$ | H |
| (1r) | $C_{16}H_{33}$ | H | H | H | $-CH(OH)-CH(OH)-CH(OH)-CH_2-OH$ | H |
| (1s) | $C_{16}H_{33}$ | H | $-CH_2OH$ | $-CH_2-OH$ | H | H |

TABLE 3

| Compound | R¹ | R² | R³ | R⁴ | R⁵ | R⁶ |
|---|---|---|---|---|---|---|
| (1t) | (zigzag chain) | H | H | H | H | H |
| (1u) | $C_{11}H_{23}$ | H | H | H | H | H |
| (1v) | $C_{13}H_{27}$ | H | H | H | H | H |
| (1w) | $C_{15}H_{31}$ | H | H | H | H | H |
| (1x) | $C_{17}H_{35}$ | H | H | H | H | H |
| (1y) | (branched zigzag chain) | H | H | H | H | H |
| (1z) | $C_9H_{19}CHCH_2$ \| $C_7H_{15}$ | | | | | |
| (1aa) | methyl-branched isostearyl | $-CH_2CH_2OH$ | H | H | H | H |
| (1ab) | methyl-branched isostearyl | $-CH_3$ | H | H | H | H |
| (1ac) | methyl-branched isostearyl | $-CH_2-\text{C}_6\text{H}_5$ | H | H | H | H |
| (1ad) | $C_{14}H_{29}$ | H | $-CH_2OH$ | $-CH_3$ | H | H |
| (1ae) | $C_{14}H_{29}$ | H | $-CH_2OH$ | $-CH_2OH$ | H | H |
| (1af) | $C_{14}H_{29}$ | H | H | H | $-CH_3$ | H |

Properties, melting points, and IR and NMR data of amine derivatives (1a)–(1af) obtained are as follows.

(1a) Colorless powder:
(m.p. 69.1°–69.5° C.)
IR (KBr, cm⁻¹) 3448, 2920, 2852, 1464, 1374, 1330, 1120, 1090, 1054.
¹H-NMR(CDCl₃, δ) 0.67–1.87(m, 27H), 2.53–2.90(m, 4H), 2.93–3.20(br, 3H), 3.30–4.07(m, 7H).

(1b) Colorless powder:
m.p. 52.7°–53.8° C.
IR (KBr, cm⁻¹) 3452, 2920, 2852, 1466, 1432, 1380, 1358, 1332, 1120, 1050, 870.
¹H-NMR(CDCl₃, δ) 0.63–1.97(m, 19H), 2.52–3.22(m, 7H), 3.25–4.10(m, 7H).

(1c) Colorless powder:
m.p. 60.2°–61.5° C.
IR (KBr, cm⁻¹) 3452, 2920, 2852, 1464, 1356, 1382, 1120, 1050, 958, 872.
¹H-NMR(CDCl₃, δ) 0.63–1.80(m, 23H), 2.54–2.96(m, 7H), 3.26–4.13(m, 7H).

(1d) Colorless powder:
(m.p. 70.6°–71.2° C.)
IR (KBr, cm⁻¹) 3448, 2920, 2852, 1462, 1124, 1050.
¹H-NMR(CDCl₃, δ) 0.67–1.67(m, 31H), 2.60–2.80(m, 4H), 3.10–3.90(m, 10H).

(1e) Colorless powder:
(m.p. 77.8°–78.3° C.)
IR (KBr, cm⁻¹) 3452, 2920, 2852, 1464, 1376, 1360, 1330, 1120, 1052, 868.
¹H-NMR(CDCl₃, δ) 0.67–1.90(m, 35H), 2.13–3.11(m, 7H), 3.30–4.13(m, 7H).

(1f) Colorless powder:
(m.p. 177.6°–178.9° C.)
IR (KBr, cm⁻¹) 3456, 3376, 2936, 2912, 1458, 1368, 1096, 1052, 948, 860.
¹H-NMR(CDCl₃, δ) 0.68(s, 3H), 0.84–1.72(m, 32H), 1.72–2.48(m, 7H), 2.66–2.96(m, 7H), 3.06–3.26(m, 1H), 3.36–3.58(m, 2H), 3.63(bt, J=5.0 Hz, 2H), 3.80–3.96(m, 1H), 5.32–5.38(m, 1H).

(1g) Light yellow paste:
IR (NaCl, cm⁻¹) 3440, 2924, 2856, 1462, 1380, 1118, 1054.
¹H-NMR)CDCl₃, δ) 0.65–1.80(m, 35H), 2.38–2.92(m, 4H), 3.18–4.22(m, 10H).

(1g') Light yellow gel:
IR(NaCl, cm⁻¹) 3344, 2920, 2856, 1588, 1460, 1376, 1092.
¹H-NMR(CDCl₃, δ) 0.62–1.93(m, 35H), 2.90–3.83(m, 10H), 3.83–4.67(m, 5H).

(1h) Light yellow solid:
(m.p. 36.0°–37.2° C.)
IR (NaCl, cm⁻¹) 3344, 2928, 2856, 1462, 1352, 1326, 1112, 1058.
¹H-NMR(CDCl₃, δ) 0.76–2.33(m, 33H), 2.60–2.93(m, 4H), 3.13–4.20(m, 10H), 5.23–5.67(m, 2H).

(1i) Colorless solid:
(m.p. 77.0°–78.4° C.)
IR (KBr, cm⁻¹) 3308, 2874, 1596, 1496, 1440, 1244, 1062, 1044, 956, 856, 754, 698.
¹H-NMR(CDCl₃, δ) 2.70–2.90(m, 4H), 3.44(bs, 3H), 3.70(bt, J=5.0 Hz, 2H), 3.94(d, J=5.3 Hz, 2H), 4.06–4.20(m, 1H), 6.85–7.00 (m, 3H), 7.22–7.34(m, 2H).

(1j) Light yellow oil:
  IR (NaCl, cm$^{-1}$) 3364, 2924, 2856, 1460, 1376, 1118, 1076, 1040.
  $^1$H-NMR(CDCl$_3$, δ) 0.89(t, J=6.5 Hz, 3H), 1.10–1.75(m, 24H), 2.34–2.95(m, 6H), 3.24–4.06(m, 9H), 4.61(br, 3H).

(1k) Light yellow oil:
  IR (NaCl, cm$^{-1}$) 3404, 2928, 2856, 1462, 1118, 1080, 1036, 752.
  $^1$H-NMR(CDCl$_3$, δ) 0.88(t, J=6.5 Hz, 3H), 1.12–1.72(m, 24H), 2.30–2.77(m, 7H), 3.09(br, 2H), 3.33–3.54(m, 4H), 3.60–3.70(m, 2H), 3.85–4.00(m, 1H).

(1l) Light yellow oil:
  IR (NaCl, cm$^{-1}$) 3404, 2928, 2856, 1456, 1378, 1114, 1068, 736, 698.
  $^1$H-NMR(CDCl$_3$, δ) 0.89(t, J=6.5 Hz, 3H), 1.09–1.70(m, 27H), 2.55–3.08(m, 6H), 3.25–4.04(m, 9H), 7.18–7.40(m, 5H).

(1m) Colorless solid:
  (m.p. 88.9°–90.2° C.)
  IR (KBr, cm $-1$) 3360, 2924, 2852, 1468, 1348, 1244, 1126, 1100, 1084, 1042.
  $^1$H-NMR(CDCl$_3$, δ) 0.88(t, J=6.5 Hz, 3H), 1.20–1.80(m, 27H), 2.27–2.86(m, 7H), 3.30–4.02(m, 11H), 4.57(br, 5H).

(1n) Light yellow oil:
  IR (NaCl, cm$^{-1}$) 3388, 2920, 2856, 1470, 1110, 1074, 1036, 1026, 744, 702.
  $^1$H-NMR(CDCl$_3$, δ) 0.88(t, J=6.5 Hz, 3H), 1.16–1.72(m, 28H), 2.46–2.82(m, 4H), 3.22–4.00(m, 13H).

(1o) Light yellow oil:
  IR (NaCl, cm$^{-1}$) 3352, 2928, 2856, 1458, 1118, 1088, 1054, 1042, 756, 702.
  $^1$H-NMR(CDCl$_3$, D$_2$O, δ) 0.86(t, J=6.5 Hz, 3H), 1.08–1.80(m, 28H), 2.38–2.90(m, 4H), 3.13–4.13(m, 13H), 7.14(br, 5H).

(1p) Colorless powder:
  (m.p. 100.5°–102.2° C.)
  IR (KBr, cm$^{-1}$) 3388, 2920, 2852, 1470, 1352, 1124, 1076.
  $^1$H-NMR(CDCl$_3$, δ) 0.88(t, J=6.5 Hz, 3H), 1.05–1.67(m, 24H), 1.68–2.20(m, 4H), 2.58–2.94(m, 4H), 3.31–3.96(m, 8H).

(1q) Colorless powder:
  (m.p. 98.4°–99.5° C.)
  IR (KBr, cm$^{-1}$) 3440, 2920, 2852, 1468, 1344, 1124, 1096, 1064.
  $^1$H-NMR(CDCl$_3$, δ) 0.88(t, J=6.5 Hz, 3H), 1.13–1.67(m, 28H), 2.30–2.97(m, 8H), 3.30–4.00(m, 8H).

(1r) Colorless powder:
  (m.p. decomposed, not measurable)
  IR (NaCl, cm$^{-1}$) 3352, 2928, 2856, 1470, 1458, 1118, 1088, 1054, 1042, 756, 702.
  $^1$H-NMR(CDCl$_3$, D$_2$O, δ) 0.86(t, J=6.5 Hz, 3H), 1.08–1.80(m, 28H), 2.38–2.90(m, 4H), 3.13–4.13(m, 13H), 7.14(br, 5H).

(1s) Colorless powder:
  (m.p. 85.7°–87.1° C.)
  IR (KBr, cm$^{-1}$) 3488, 2924, 2852, 1470, 1334, 1120, 1036.
  $^1$H-NMR(MeOH-d$_4$, δ) 0.67–1.93(m, 31H), 2.50–2.94(m, 2H), 3.17–3.98(m, 13H).

(1t) Colorless powder:
  (m.p. 50.3°–51.2° C.)
  IR (KBr, cm$^{-1}$) 3448, 2920, 2848, 1464, 1425, 1359, 1116, 1047, 957, 912, 867.
  $^1$H-NMR(CDCl$_3$, δ) 1.18–1.75(m, 14H), 1.95–2.12(m, 2H), 2.55–2.84(m, 4H), 3.02 (brs, 3H), 3.32–3.52(m, 4H), 3.60–3.74(m, 2H), 3.82–3.98(m, 1H), 4.85–5.07(m, 2H), 5.68–5.94(m, 1H).

(1u) Colorless powder:
  (m.p. 61.2°–62.1° C.)
  IR (KBr, cm$^{-1}$) 3448, 2920, 2852, 1466, 1120, 1052,
  $^1$H-NMR(CDCl$_3$, δ) 0.80–0.98(m, 3H), 1.18–1.70(m, 18H), 2.54–2.85(m, 4H), 3.05–4.00(m, 10H).

(1v) Colorless powder:
  (m.p. 67.4°–68.4° C.)
  IR (KBr, cm$^{-1}$) 3444, 2920, 2848, 1464, 1358, 1332, 1120, 1090, 1050, 952, 868, 722.
  $^1$H-NMR(CDCl$_3$, δ) 0.88(t, J=6.24 Hz, 3H), 1.10–1.70(m, 22H), 2.54–3.20(m, 7H), 3.30–3.52(m, 4H), 3.58–3.74(m, 2H), 3.80–3.98(m, 1H).

(1w) Colorless powder:
  (m.p. 72.2°–73.4° C.)
  IR (KBr, cm$^{-1}$) 3448, 2920, 2852, 1464, 1378, 1328, 1122, 1052, 956, 866, 720.
  $^1$H-NMR(CDCl$_3$, δ) 0.88(t, J=6.19 Hz, 3H), 1.08–1.70(m, 26H), 2.50–3.20(m, 7H), 3.28–3.50(m, 4H), 3.58–3.72(m, 2H), 3.80–3.98(m, 1H).

(1x) Colorless powder:
  (m.p. 77.4°–78.0° C.)
  IR (KBr, cm$^{-1}$) 3440, 3312, 2916, 2852, 1464, 1378, 1356, 1330, 1120, 1052, 954, 868, 720.
  $^1$H-NMR(CDCl$_3$, δ) 0.88(t, J=6.24 HZ, 3H), 1.10–1.70(m, 30H), 2.50–3.25(m, 7H), 3.32–3.52(m, 4H), 3.62–3.72(m, 2H), 3.82–3.98(m, 1H).

(1y) Light yellow oil:
  IR (NaCl, cm$^{-1}$) 3388, 2926, 2856, 1461, 1377, 1110.
  $^1$H-NMR(CDCl$_3$, δ) 0.70–0.97(m, 15H), 0.98–1.76(m, 20H), 2.56–2.73(m, 4H), 3.29–3.59(m, 4H), 3.62–4.10(m, 6H).

(1z) Light yellow oil:
  IR (NaCl, cm$^{-1}$) 3296, 2924, 2856, 1458, 1374, 1118, 1052, 940, 884.
  $^1$H-NMR(CDCl$_3$, δ) 0.70–0.98 (m, 15H), 0.98–1.78 (m, 20H), 2.56–2.92(m, 4H), 3.30–3.60(m, 4H), 3.62–4.10(m, 6H).

(1aa) Light yellow oil:
  IR (NaCl, cm$^{-1}$) 3356, 2924, 2856, 1464, 1376, 1122, 1070.
  $^1$H-NMR(CDCl$_3$, δ) 0.78–1.00(m, 6H), 1.00–1.75(m, 29H), 2.32–2.88(m, 6H), 3.30–4.00(m, 9H), 4.90(brs, 3H).

(1ab) Light yellow oil:
  IR (NaCl, cm$^{-1}$) 3424, 2928, 2856, 1460, 1378, 1116, 1040.
  $^1$H-NMR(CDCl$_3$, δ) 0.72–0.96(m, 6H), 1.00–1.76(m, 29H), 2.33(s, 3H), 2.36–2.72 (m, 4H), 3.30–3.52(m, 6H), 3.57–3.68(m, 2H), 3.82–3.96(m, 1H).

(1ac) Light yellow oil:
  IR (NaCl, cm$^{-1}$) 3388, 2924, 2856, 1454, 1370, 1118.
  $^1$H-NMR(CDCl$_3$, δ) 0.63–1.92(m, 35H), 2.40–4.06(m, 15H), 7.18(brs, 5H).

(1ad) Colorless powder:

(m.p. 93.6°–94.5° C.)

IR (KBr, cm$^{-1}$) 3404, 2924, 2852, 1470, 1350, 1120, 1102, 1050.

$^1$H-NMR(CDCl$_3$, δ) 0.80–1.00(m, 6H), 1.10–1.68(m, 24H), 2.45–2.74(m, 2H), 3.20–3.64(m, 12H), 3.78–3.98(m, 1H).

(1ae) Colorless powder:

(m.p. 84.4°–85.4° C.)

IR (KBr, cm$^{-1}$) 3308, 2924, 2856, 1466, 1378, 1114.

$^1$H-NMR(CDCl$_3$, δ) 0.80–1.00(m, 3H), 1.10–1.70(m, 24H), 2.56–2.74(m, 2H), 3.24–3.74(m, 15H), 3.88–4.06(m, 1H).

(1af) Colorless powder:

(m.p. 79.5°–81.2° C.)

IR (KBr, cm$^{-1}$) 3424, 3148, 2914, 2848, 1467, 1347, 1110, 1029, 969, 870.

$^1$H-NMR(CDCl$_3$, δ) 0.88(t, J=6.4 Hz, 3H), 1.15(d, J=6.1 Hz, 3H), 1.21–1.73(m, 24H), 2.38–2.90(m, 7H), 3.30–3.60(m, 4H), 3.72–4.01(m, 2H).

EXAMPLE 1

Effect of amine derivative to wrinkles of hairless mouse produced by UVB radiation (1) UVB light was irradiated on hairless mice (HR/ICR, 9 week age at the start of the experiment), 3 times a week, using 6 Toshiba health light lamps 20SE. The energy amount was measured by UV-Radiometer UVR-305/365D manufactured by Tokyo Optical Co. One irradiation was less than 1 MED; 65 mj with an energy amount of 0.28 mW/cm$^2$. After confirming production of wrinkles on the bank of the hairless mice by irradiation of 20 weeks, the mice were divided into 8 groups. 80 μl of a 0.005% ethanol solution of amine derivative (1g) was applied for 6 weeks, 5 times a week. For a control group, 80 μl of ethanol was applied in the same way.

After the completion of the application, the degree of wrinkles was evaluated by the following criterion (wrinkle index). The results are shown in Table 4.

(Wrinkle degree)
1. No coarse wrinkle.
2. A few shallow coarse wrinkles across back.
3. Same coarse wrinkles across back.
4. Several deep coarse wrinkles across back.

TABLE 4

| Group | Wrinkle index |
|---|---|
| Control | 3.75 ± 0.09 |
| Amine derivative (1g) | 2.94 ± 0.09 |

As clear from Table 4, the application of amine derivative (1g) could extinguish wrinkles developed on the back of hairless mice.

(2) In order to analyze the details of wrinkles, skin replicas with a diameter of 1 cm$^2$ were taken from 3 sites for each mouse, by using a hydrophilic exaflex vinyl silicone image duplicator. The replicas were horizontally placed to irradiate a light from a direction of 30° in angle. Percentage of shades emerged with by wrinkles in total area of the replica was determined by an image analyzer. The results are shown in Table 5.

TABLE 5

| Group | Area percentage by image analysis (%) |
|---|---|
| Control | 6.42 ± 0.63 |
| Amine derivative (1g) | 2.71 ± 0.35 |

As can be seen from Table 5, the application of amine derivative (1g) could extinguish wrinkles developed on the back of hairless mice.

EXAMPLE 2

Effect of amine derivatives (1) to the suppression of epidermal keratinized cell DNA synthesis (1) Method a) Cultivation of human epidermal keratinocytes Human epidermal keratinocytes (trademark: Epipack) sold by Kurabo Co. was used. A medium for human normal keratinocytes (trademark: K-GM) sold by the same company was used for the subsistence and subculture of the cells.

b) Measurement of DNA synthesis (Measurement of thymidine incorporation)

Keratinocytes cultivated under the proliferating conditions in a 24-well plate were used. First, the medium in each well was removed by aspiration, and replaced by the addition of 450 μl of K-GM to which no pituitary extract was added, followed by the addition of amine derivatives (1a)–(1af) obtained in above Synthetic Examples. Then, after the addition of 0.2 μCi/ml [$^3$H]-thymidine over time, the mixture was incubated for 4 hours. The supernatant was removed by aspiration and the residue was washed 3 times with PBS(–), followed by the addition of 500 μl of 2N NaOH. After incubation at 37° C. for 10 minutes, the mixture was neutralized with the equivalent amount of 2N HCl. After the addition of 4 ml of ice-cold 10% trichloroacetic acid, the mixture was allowed to stand for 30 minutes.

Precipitate was collected by filtration through a glass filter and washed 3 times with 3 ml of ice-cold 10% trichloroacetic acid. The glass filter was washed once more with 3 ml of ice-cold ethanol, dried in air, and submitted to the measurement of the radio activity by a liquid scintillation counter to calculate thymidine taken into the cells.

(2) Results

Figure 2:
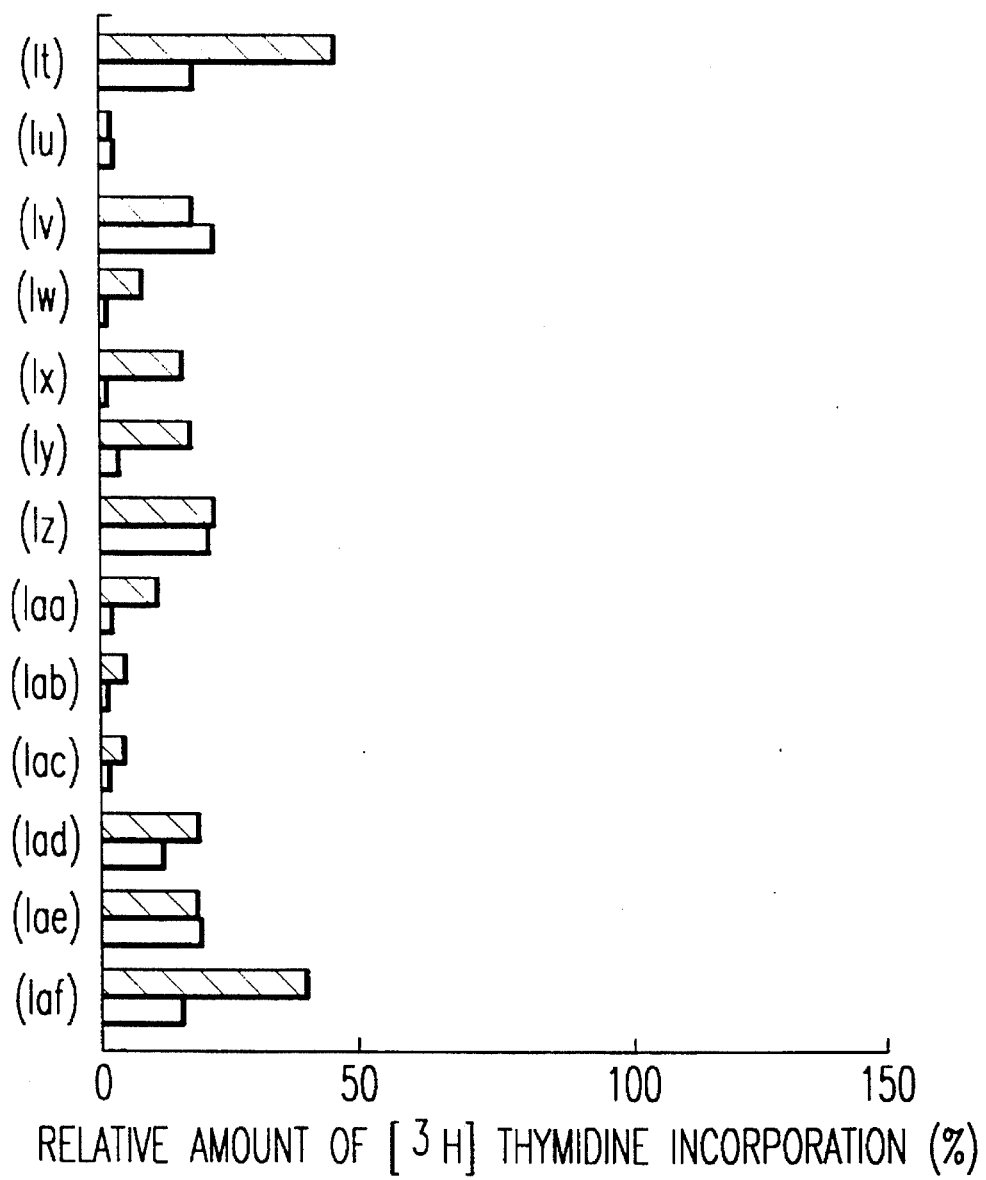

FIGS. 1 and 2 show the relative amount of [$^3$H] thymidine incorporation (%) when amine derivatives (1a)–(1af) at 10 μM (upper row) and 100 μM (lower row).

These figures clearly show that the thymidine intake is remarkably reduced by the addition of the above amine derivatives, that is, synthesis of epidermal keratinocytes DNA is inhibited.

EXAMPLE 3

Effect of amine derivatives on transglutaminase activity of epidermal keratinocytes (1) Measurement of transglutaminase activity Keratinocytes cultivated under the proliferating conditions in a 6-well plate were used. The medium in each well was removed by aspiration, and replaced by the addition of 2 ml of K-GM to which no pituitary extract was added, followed by the addition of amine derivatives (1a) and (1g). After 24 hours, each well was washed 3 times with PBS(–). Cells were collected by releasing them from the wells by rubber policeman. The cell suspension thus obtained was centrifuged at 2,500 rpm for 10 minutes to collect a precipitate. After the addition of 200 μl of buffer solution (a) [10 mM Tris-HCl buffer, 10 mM DTT, 0.5 mM EDTA; pH 7.4], the mixture was ultrasonicated 2 times, for 1 minute each time. The suspension thus obtained was subjected to ultracentrifuge for 30 minutes at 25,000 rpm to obtain a supernatant. The supernatant was divided into portions of a specified amount. To each portion was added a reaction solution [a mixed solution of 300 mM Tris-HCl buffer, pH 8.1; 60 mM $CaCl_2$, 100 μl; 30 mM DTT, 100 μl; distilled water containing 540 μg of dimethylcasein, 100 μl; 12 mM putrescine, 50 μl; 2.5 μCl[$^{14}$C]-putrescine, 50 μl; and distilled water, 100 μl] and the mixture was incubated at 37° C. for 1 hour. Then, after the addition of 600 μl of 10% trichloroacetic acid, the mixture was allowed to stand still for 30 minutes. The precipitate was collected by using 0.45 μm nitrocellulose membrane. The membrane was washed with 15 ml of ice-cooled 5% trichloroacetic acid (containing 1% putrescine). The radio activity of the substance on the membrane was measured by a liquid scintillation counter.

(2) Results

Figure 3:
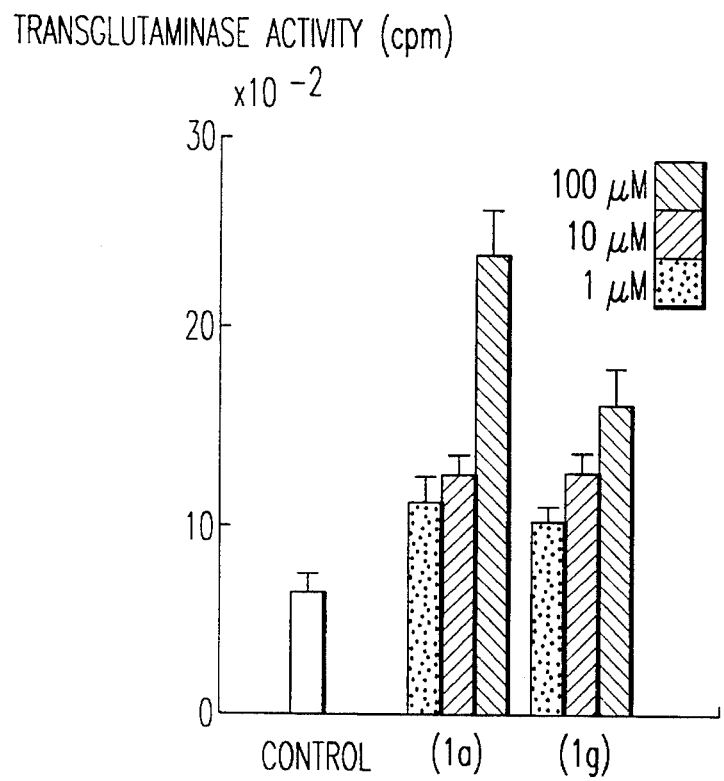
FIG. 3 is a drawing showing changes in the transglutaminase activity due to the addition of the amine derivative of Example 2.

FIG. 3 shows the transglutaminase activities (cpm) when 1 μM, 10 μM, and 100 μM of amine derivatives were added. The activity values increase to a value as much as about 3.0 times for the value of the control along with the increase in the amounts of amine derivatives added. This is an evidence that said amine derivatives possess a differentiation inducing activity for keratinocytes.

EXAMPLE 4

Effect of amine derivatives on the control of dermal thickening (1) Method

UVB (2–3 Med) was irradiated to hair-cut ears of 25 white guinea pigs, aged 4–6 weeks, and starting immediately after the irradiation squalane solutions containing 0.05% amine derivatives (1a) or (1g) were applied, once a day, for 1 week.

After 1 week, ears of guinea pigs were cut out to prepare skin organization specimens. A microscopic photograph was taken for each organization sample to measure the epidermal thicknesses, thus evaluating the effects of the sample compounds on the control of thickening by the UVB irradiation.

(2) Results

Figure 4:
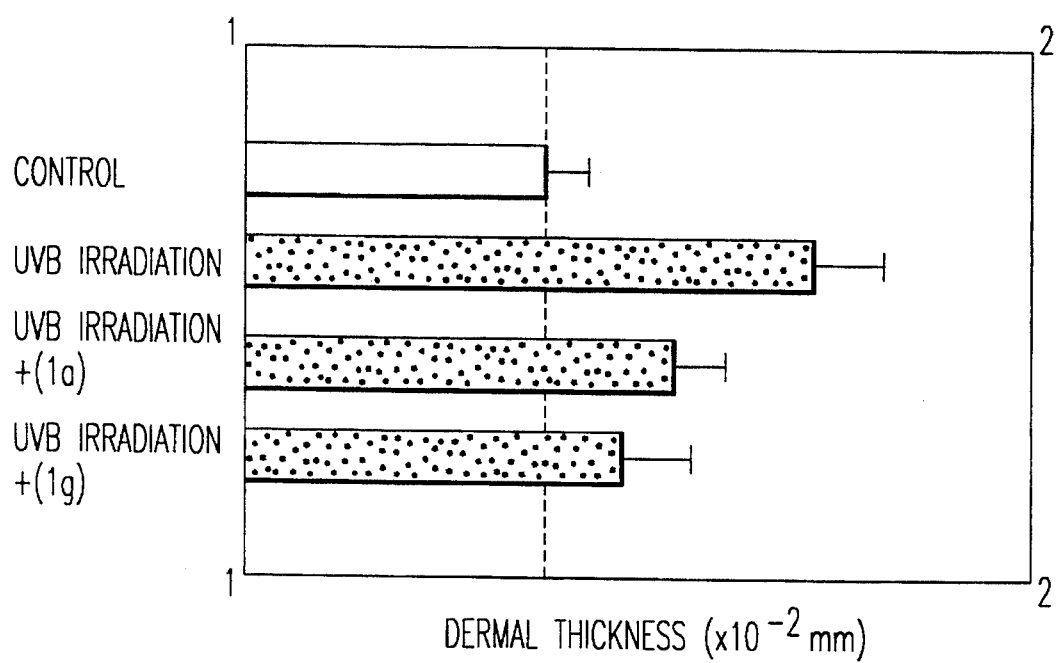
FIG. 4 is a drawing showing changes in the skin thickness due to UVB irradiation and the addition of the amine derivative of Example 3.

FIG. 4 shows the results of the dermal thickness measurement on a sample to which UVB was irradiated, a sample to which amine derivative (1a) was applied after the UVB irradiation, and a sample to which amine derivative (1g) was applied after the UVB irradiation. The concentration of each sample was 0.05%. The results demonstrate that these amine derivatives have an effect of controlling epidermal thickening.

EXAMPLE 5

Preparation of W/O Cream

|      |                          | % by weight |
|------|--------------------------|-------------|
| (1)  | Amine Derivative (1a)    | 0.01        |
| (2)  | Cholesterol              | 0.5         |
| (3)  | Cholesterol isostearate  | 1.0         |
| (4)  | Polyether-modified silicone | 1.5      |
| (5)  | Cyclic silicone          | 20.0        |

-continued

|      |                          | % by weight |
|------|--------------------------|-------------|
| (6)  | Methylphenyl polysiloxane | 2.0        |
| (7)  | Methyl polysiloxane      | 2.0         |
| (8)  | Magnesium sulfate        | 0.5         |
| (9)  | 55% Ethanol              | 5.0         |
| (10) | Carboxymethyl chitin (Chitin liquid HV, manufactured by Ichimaru Farcos Co.) | 0.5 |
| (11) | Purified water           | Balance     |

(1)–(7) were heated to 80° C. to dissolve. (8)–(11) were added to the mixture and homogeneously blended to produce a W/O cream.

EXAMPLE 6

Preparation of O/W Cream

|      |                          | % by weight |
|------|--------------------------|-------------|
| (1)  | Polyoxyethylene (10) hydrogenated castor oil | 1.0 |
| (2)  | Sorbitan monostearate    | 0.5         |
| (3)  | Sodium stearoyl methyltaurine | 0.5    |
| (4)  | Cetostearyl alcohol      | 2.0         |
| (5)  | Stearic acid             | 1.8         |
| (6)  | Amine Derivative (1g)    | 0.001       |
| (7)  | Cholesterol              | 1.5         |
| (8)  | Cholesteryl isostearate  | 1.0         |
| (9)  | Dicapric acid neopentyl glycol | 8.0   |
| (10) | Methyl polysiloxane      | 5.0         |
| (11) | Glycerine                | 5.0         |

(1)–(10) were heated to 80° C. to dissolve, (11)–(12) were added to the mixture and homogeneously blended to produce an O/W cream,

EXAMPLE 7

Preparation of moisturizing sunscreen cream

|      |                          | % by weight |
|------|--------------------------|-------------|
| (1)  | Amine Derivative (1g)    | 0.005       |
| (2)  | Silicone coated zinc oxide | 7.0       |
| (3)  | 2-Ethylhexyl p-methoxycinnamate | 3.0  |
| (4)  | Cholesteryl isostearate  | 1.0         |
| (5)  | Polyether-modified silicone | 2.0      |
| (6)  | Methyl polysiloxane      | 5.0         |
| (7)  | Cyclic silicone          | 15.0        |
| (8)  | Magnesium sulfate        | 1.0         |
| (9)  | Glycerine                | 5.0         |
| (10) | Purified water           | Balance     |

(1)–(7) were heated to 80° C. to dissolve. (8)–(10) were added to the mixture and homogeneously blended to produce a moisturizing sunscreen cream.

EXAMPLE 8

Preparation of ointment

|      |                          | % by weight |
|------|--------------------------|-------------|
| (1)  | Amine Derivative (1a)    | 0.005       |
| (2)  | White petrolatum         | Balance     |
| (3)  | Cholesteryl isostearate  | 3.0         |
| (4)  | Liquid paraffin          | 10.0        |

21
-continued

|  | % by weight |
|---|---|
| (5) Glyceryl ether | 1.0 |
| (6) Glycerine | 10.0 |

(1)–(6) were heated to 80° C. to dissolve and cooled to produce an ointment.

EXAMPLE 9

Preparation of face pack

|  | % by weight |
|---|---|
| (1) Amine Derivative hydrochloride (1g') | 0.05 |
| (2) Polyvinyl alcohol | 15.0 |
| (3) Sodium carboxymethyl cellulose | 5.0 |
| (4) Propylene glycol | 3.0 |
| (5) Ethanol | 8.0 |
| (6) Purified water | 67.5 |
| (7) Perfume | 0.5 |
| (8) Preservative, antioxidant | q.s. |

(1)–(8) were heated to 70° C. to dissolve and cooled to produce a face pack.

Compositions for external skin care prepared in Examples 5–9 were all exhibited excellent effects of suppressing production of and extinction of wrinkles. They were effective in controlling incomplete keratinization, skin thickening, and abnormal lipid metabolism, and further in the restoration and constant maintenance of normal skin functions. Furthermore, these compositions did not cause red spots on the skin to develop, nor they were irritative to the skin.

Industrial Applicability

The composition for external skin car of the present invention has an excellent effect of suppressing generation of or diminishing wrinkles, and exhibits an action of controlling incomplete keratinization, skin thickening, and abnormal lipid metabolism. In addition the composition is a highly safe material.

We claim:

1. A composition for external skin care comprising in an effective amount for reducing wrinkles and/or improving keratinization of the skin at least one amine derivative of the following formula:

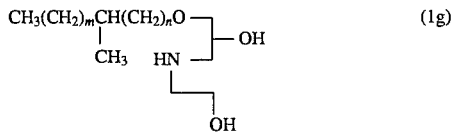

(1g)

wherein m+n is 11–17, m is 4–10 and n is 5–11.

2. The composition as claimed in claim 1, wherein said composition contains more than one compound of formula 1g, said more than one compound having a distribution peak at m=7 and n=8.

3. A method of improving wrinkles characterized by applying to the skin an amine derivative of the following formula (1),

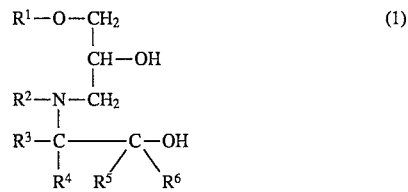

wherein $R^1$ is a linear, branched, or cyclic saturated or unsaturated hydrocarbon group having 4–40 carbon atoms, and $R^2$, $R^3$, $R^4$, $R^5$, and $R^6$ are individually a hydrogen atom or a hydrocarbon group having 1–10 carbon atoms, which may be substituted or unsubstituted by 1 or more hydroxy groups; or an acid addition salt thereof.

4. A method of improving wrinkles according to claim 3, wherein $R^1$ in said formula (1) is a linear, branched, or cyclic saturated or unsaturated hydrocarbon group having 4–40 carbon atoms, $R^2$, $R^3$, $R^4$, $R^5$, and $R^6$ are individually a hydrogen atom.

5. A method of improving wrinkles according to claim 3, wherein $R^1$ in said formula (1) is a group represented by the following formula,

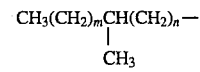

wherein m+n is 11–17, m is 4–10, and n is 5–11, and $R^2$, $R^3$, $R^4$, $R^5$, and $R^6$ are individually a hydrogen atom.

6. A method of improving keratinization of the skin characterized by applying an amine derivative of the following formula (1),

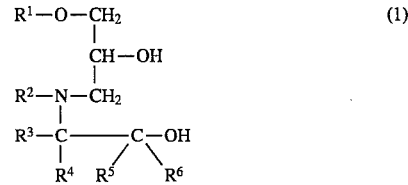

wherein $R^1$ is a linear, branched, or cyclic saturated or unsaturated hydrocarbon group having 4–40 carbon atoms, and $R^2$, $R^3$, $R^4$, $R^5$, and $R^6$ are individually a hydrogen atom or a hydrocarbon group having 1–10 carbon atoms, which may be substituted or unsubstituted by 1 or more hydroxy groups; or an acid addition salt thereof, to the skin.

7. A method of improving keratinization of the skin according to claim 6, wherein $R^1$ in said formula (1) is a linear, branched, or cyclic saturated or unsaturated hydrocarbon group having 4–40 carbon atoms, $R^2$ is a hydrogen atom, or a lower alkyl or a lower hydroxyalkyl group, and $R^3$, $R^4$, $R^5$, and $R^6$ are individually a hydrogen atom.

8. A method of improving keratinization of the skin according to claim 6, wherein $R^1$ in said formula (1) is a group represented by the following formula,

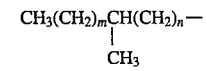

wherein m+n is 11–17, m is 4–10, and n is 5–11, and $R^2$, $R^3$, $R^4$, $R^5$, and $R^6$ are individually a hydrogen atom.

* * * * *